(12) United States Patent
Zeller et al.

(10) Patent No.: US 7,267,832 B2
(45) Date of Patent: Sep. 11, 2007

(54) AMORPHOUS WATER-SOLUBLE CALCIUM CITRATE SALTS AND METHOD OF MAKING AND USING SAME

(75) Inventors: Bary Lyn Zeller, Glenview, IL (US); Robert Charles Dinwoodie, Glenview, IL (US); Ahmad Akashe, Mundelein, IL (US); Cheryl Jean Baldwin, Mundelein, IL (US)

(73) Assignee: Kraft Foods Holdings, Inc., Northfield, IL (US)

( * ) Notice: Subject to any disclaimer, the term of this patent is extended or adjusted under 35 U.S.C. 154(b) by 603 days.

(21) Appl. No.: 10/781,106

(22) Filed: Feb. 18, 2004

(65) Prior Publication Data

US 2005/0181096 A1    Aug. 18, 2005

(51) Int. Cl.
*A23L 1/304* (2006.01)
(52) U.S. Cl. .................. 426/74; 426/384; 426/471; 426/518; 426/648
(58) Field of Classification Search ................ 426/74, 426/648, 384, 471, 518
See application file for complete search history.

(56) References Cited

U.S. PATENT DOCUMENTS 4,851,221 A    7/1989   Pak et al.
5,208,372 A    5/1993   Vidal et al.
6,235,322 B1   5/2001   Lederman
2002/0114868 A1* 8/2002 Lederman ................ 426/74
2002/0122866 A1   9/2002 Palaniappan et al.
2006/0251765 A1* 11/2006 Lederman ................ 426/74

FOREIGN PATENT DOCUMENTS

GB           597936         2/1948
WO        WO88/03762        6/1988

* cited by examiner

*Primary Examiner*—Helen Pratt
(74) *Attorney, Agent, or Firm*—Fitch, Even, Tabin & Flannery

(57) ABSTRACT

Amorphous water-soluble calcium citrate salts having a mole ratio of calcium to citrate of less than 2.5:2, and powdered beverage mixes and liquid compositions fortified with these amorphous water-soluble calcium citrate salts as a calcium source, are provided. Liquid compositions fortified with calcium citrate according to this invention have superior dispersability, solubility, appearance, and storage stability. These liquid compositions are prepared by new methods that provide and preserve a stable amorphous character in the dry powdered product salts. The present invention also is directed to a method of administering such calcium citrate-fortified liquid compositions to increase the dietary calcium intake in individuals.

4 Claims, No Drawings

AMORPHOUS WATER-SOLUBLE CALCIUM CITRATE SALTS AND METHOD OF MAKING AND USING SAME

FIELD OF THE INVENTION

The present invention generally relates to amorphous water-soluble calcium citrate salts and foods and beverages (including powdered drink mixes and liquid compositions) fortified with such calcium citrate salts.

BACKGROUND OF THE INVENTION

The mineral calcium forms an important part of proper nutrition. Calcium is essential for bone and tooth formation. Approximately 99 percent of the calcium in the body is stored in bones and teeth, while the remaining 1 percent is present in the blood and soft tissues as circulating calcium (generally in the form of $Ca^{+2}$ ions). The circulating calcium is essential for proper muscular contraction, blood clotting, and nerve transmission functions. In addition to their structural role, bones provide an emergency supply of circulating calcium.

Osteoporosis is a widespread problem, afflicting approximately twenty million women and five million men in the United States to some degree. Post-menopausal women typically lose about 0.7 to 2 percent of their bone mass per year, while men lose about 0.5 to 0.7 percent. Consequently, between the ages of 45 and 70, women and men can lose about 30 and 15 percent, respectively, of their skeletal mass. In the United States more than one million bone fractures occur annually in women 45 years or older; in about 70 percent of these cases, osteoporosis plays a significant role. There are approximately 190,000 hip fractures annually in the United States; hip fractures are the second leading cause of death in people 47-74 years of age. More recent studies have suggested that reduced calcium intake in children may result in increased risk for osteoporosis later in life.

Dietary calcium supplementation and fortification is recognized in the health field as a convenient and safe approach for addressing calcium deficits. The Recommended Dietary Allowances (RDA's) for calcium by the National Academy of Sciences are 1,200 mg/day for adults 51+years old; 1,000 mg/day for adults 19-50 years old; 1,300 mg/day for children 9-18 years old; 800 mg/day for children 4-8 years old; and 500 mg/day children 1-3 years old. The US Daily Value (DV) for calcium is 1000 mg/day for all individuals; this reference value is typically used to establish nutritional calcium levels in food products. The Food and Drug Administration (FDA) permits foods and beverages containing at least 100 mg calcium per serving to be labeled as a "good source of calcium"; those containing at least 200 mg calcium per serving may be labeled as an "excellent source of calcium."

However, many conventional dietary sources of calcium contain lower than desired levels of calcium. Simply increasing the amount of calcium using conventional fortification techniques to provide more nutritionally desirable levels often unfavorably impacts the food product's pH, flavor, texture, appearance, and/or cost. Another problem is that many conventional dietary sources of calcium have low solubility or dispersability in water and tend to precipitate in aqueous solutions, forming turbid fluids and/or sediments which can impart undesirable chalky or gritty attributes in beverages. Such quality defects can decrease consumer acceptance and limit consumption, thereby reducing the nutritional benefits afforded by such calcium-containing products.

Among the conventional calcium citrate compounds most commonly used in foods, crystalline tricalcium dicitrate (i.e., tricalcium citrate or "TCC"; calcium:citrate mole ratio of 3:2) has limited utility in beverage applications since it is virtually insoluble in water. The TCC ingredient most commonly used in food fortification is crystalline TCC tetrahydrate. Although this material contains a high level of calcium (about 21 percent), it only provides about 6 mg of soluble calcium per fluid ounce of water at room temperature due to its low solubility (i.e., less than 0.1 percent in water at room temperature); this level of fortification would provide only about 5 percent of the U.S. DV for calcium in soluble form; simply attempting to add greater amounts to water would result in immediate precipitation. Other sparingly soluble calcium citrates like crystalline monocalcium dicitrate (i.e., monocalcium citrate or "MCC"; calcium:citrate mole ratio of 1:2) and crystalline dicalcium dicitrate (i.e., dicalcium citrate or "DCC"; calcium:citrate mole ratio of 2:2) also have limited utility due to slow dissolution, incomplete dispersion, or undesirable sedimentation.

U.S. Pat. No. 4,851,221 describes a dry powdered premix of citric acid and calcium hydroxide in a mole ratio of between about 0.6 to about 1.5, which is combined directly with a potable liquid to make a solution reported to have enhanced calcium bioavailability. The premix, after being dissolved in water, is reported to form calcium citrate precipitates within several hours after dissolution in water unless the pH is below about 3.5. The relatively low pH value required to avoid precipitation of the calcium citrate is a significant limitation on the usefulness of the premixes described therein. Moreover, calcium hydroxide is strongly alkaline and can cause degradation and/or discoloration of many commonly used food ingredients (especially if there is exposure to moisture during storage), thereby leading to a poor quality product with a reduced shelf life.

U.S. Patent Application No. 2002/0122866 describes a method and apparatus for producing a calcium fortified liquid beverage by forming a solution containing a soluble calcium salt of an organic acid and immediately blending with a liquid beverage in a continuous manner to avoid formation and precipitation of insoluble salts. No soluble calcium citrate or other salts in dried form were disclosed.

Calcium salts of organic acids have been used in food processing. U.S. Pat. No. 5,208,372 describes a solid calcium citrate anti-caking agent that is a water insoluble crystalline calcium citrate salt at ambient temperature having a calcium:citrate ratio of 2.5:2 to 2.95:2, and which also is said to be useful in powdered soft drinks sweetened with fructose. U.S. Pat. No. 5,219,602 describes an aqueous dispersion containing the crystalline calcium citrate salt having a calcium:citrate ratio of 2.5:2 to 2.95:2, which can be used to opacity and whiten food compositions. The insoluble crystalline calcium citrate salts described in these patents are formed by combining a calcium compound with citric acid in water and allowing adequate time for the reaction product to solidify before drying.

U.S. Pat. No. 6,235,322 describes highly soluble and stable mineral supplements containing calcium and magnesium. In particular, a fiber-free calcium/magnesium material is provided by solubilizing a calcium/magnesium mixture in an aqueous acid solution and drying the reaction product. The use of magnesium is reported to increase calcium solubility and help to provide adequate time for solutions to solidify prior to freeze drying or tray drying. Numerous specific examples of salts other than calcium citrates are provided.

As can be appreciated, there remains a need for approaches for fortifying instant and ready-to-drink (RTD) beverages with safe, convenient, and compatible forms of nutritional high-calcium salts that can provide calcium at high dietary levels and which provide improved solubility and increased shelf life stability. The present invention fulfills these, as well as other needs and objectives, as will be apparent from the following description of embodiments of the present invention.

SUMMARY OF THE INVENTION

This invention provides new amorphous water-soluble calcium citrate salts having a mole ratio of calcium to citrate of less than 2.5:2. These new amorphous calcium citrate salts should have enhanced stability and bioavailability relative to currently available calcium salts. These new amorphous water-soluble calcium citrate salts, which can be produced with high calcium levels, have enhanced dispersability, solubility, and stability in water relative to currently available calcium citrate salts and other commercially available high calcium salts (e.g., calcium fumarate, calcium carbonate, calcium phosphate, and the like). The present water-soluble amorphous calcium citrate salts are also useful as calcium fortifying agents that are rapidly and wholly dissolved in aqueous compositions. These amorphous water-soluble calcium citrate salts are especially useful when incorporated into ready-to-drink ("RTD") liquid compositions or powdered beverage mixes which may be reconstituted in water to provide beverages. Indeed, it has been surprisingly found that these amorphous water-soluble calcium citrate salts can significantly improve the appearance and extend the shelf life of liquid compositions such as acidified RTD beverages as compared to the use of conventional calcium citrate salts.

For purposes herein, "amorphous" means noncrystalline (i.e., the compound lacks a distinct crystalline structure). Crystalline substances often contain relatively small amounts of non-crystalline matter and such structural defects do not detract from classification of these substances as crystalline since the physical properties of these substances are determined by their predominantly crystalline nature. Similarly, amorphous substances often contain small amounts of crystalline matter that do not significantly detract from their unique physical properties. The amorphous calcium citrate salts of the invention were produced according to new methods disclosed herein for the express purpose of preventing crystallization to the greatest extent practically possible while enabling production of these salts on a large scale using modified food processing techniques and common drying equipment. However, it should be understood that amorphous calcium citrate salts prepared according to embodiments of the invention might contain small amounts of microcrystalline matter that can be tolerated without meaningful effect on the gross physical characteristics of these unique ingredients or on the enhanced performance benefits these ingredients provide in food and beverage fortification. For purposes of this invention, a calcium citrate salt will be considered amorphous if it contains only a small amount of microcrystalline matter; typically, the amorphous calcium citrate salts of this invention contain less than about 10 percent, preferably less than about 5 percent, and more preferably less than about 1 percent, of crystalline material.

The amorphous water-soluble calcium citrate salts of embodiments of this invention rapidly dissolve in water to form clear haze-free, sediment-free liquid compositions which can provide high levels of calcium. For purposes of this invention, the calcium citrate salts of this invention are considered "water soluble" if, when dissolved in water to provide about 10 mg calcium per fluid ounce, they do not form a visible haze or sediment for at least about 2 days at ambient temperatures. Liquid compositions (e.g., RTD beverages) formulated with these salts are stable and have long shelf lives (generally greater than about 6 months when properly packaged); for purposes of this invention, shelf life refers to the period of time during which no visible precipitation or sedimentation occurs when stored at ambient temperatures. The new amorphous water-soluble calcium citrate salt remains in solution for long periods of time, thereby providing a good source of dietary calcium.

In one embodiment of the present invention, amorphous water-soluble calcium citrate salts are provided which are represented by the following formulas:

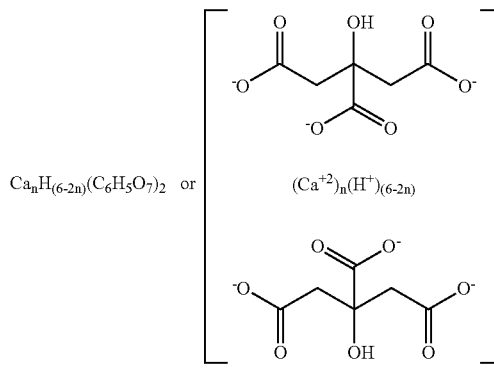

$Ca_n H_{(6-2n)}(C_6H_5O_7)_2$ or $(Ca^{+2})_n(H^+)_{(6-2n)}$ wherein "n" is a value of less than 2.5, preferably less than about 2.25, and more preferably ranging from about 1 to about 2. The "$C_6H_5O_7$" portion of the above formula represents a citrate moiety.

The calcium content of these amorphous water-soluble calcium citrate salts can easily be adjusted to obtain calcium:citrate mole ratios of less than 2.5:2 to fit a wide range of nutritional liquid and food applications. Especially preferred compositions that can be fortified with the unique amorphous water-soluble calcium citrate salts of this invention include instant beverage mixtures and RTD beverages such as, but not limited to, fruit drinks, health drinks, soft drinks, and pharmaceutical potions. However, the low-to-moderate pH and slight-to-moderate acid flavor of the present amorphous water-soluble calcium citrate salts in solution make them particularly suitable for use in acidified or naturally acidic instant or RTD beverages. The amorphous water-soluble calcium citrate salts can be used alone or in combination with other calcium sources to provide sufficient amounts of dietary calcium. Preferably, the amorphous water-soluble calcium citrate salts are used as the sole source of calcium. In addition, other essential minerals or elements (e.g., iron, zinc, potassium, and the like) can be added to enhance nutrition, modify physical-chemical properties, or improve handling. Such other essential minerals or elements can be added to the amorphous water-soluble calcium citrate salts themselves or incorporated into the amorphous water-soluble calcium citrate salts during preparation thereof.

In another aspect of the invention, these new calcium salts are prepared by a unique method that provides and preserves amorphous character in the dry powdered salt products, thereby providing a more rapidly and completely water-soluble, and water-stable (i.e., no visible precipitation or sedimentation) material. In one embodiment, the preparation method comprises neutralizing a concentrated solution of citric acid (generally at least about 1 percent citric acid and preferably about 20 to about 30 percent citric acid) with a slurry of calcium oxide or calcium hydroxide in water in the appropriate mole ratio and at a temperature of less than about 30° C. and then rapidly drying the reaction mixture. The drying must occur shortly after the reaction mixture containing the calcium citrate reaction product is formed in order to prevent transformation of the amorphous calcium citrate product into less stable, water-insoluble crystalline forms of the salt. How quickly the drying should take place depends, at least in part, on the temperature. Generally and under refrigeration conditions, such rapid drying should be carried out within about 30 minutes, and preferably within about 15 minutes, of the reaction mixture formation. Generally and under ambient conditions, such rapid drying should be carried out within about 5 minutes, and preferably within about 2 minutes, of the reaction mixture formation. Alternatively, the reaction mixture can be quickly frozen (generally within about 5 minutes, preferably within about 2 minutes, and more preferably with about 1 minute of the reaction mixture formation) for later drying; once frozen, the reaction mixture should be dried under conditions which prevent or minimize thawing. In one embodiment, a rapid drying procedure comprising freeze drying or spray drying is used. Where freeze drying is used, the frozen solid piece or pieces obtained are comminuted into a powder form after freeze drying. Where spray drying is used, the calcium and citric acid reactant preferably are chilled at the time of their admixture and up until drying.

In one embodiment of the invention, a calcium-fortified aqueous composition is provided containing greater than about 12.5 mg calcium from the amorphous calcium citrate salt per fluid ounce serving, and greater than about 100 mg calcium per eight fluid ounce (about 240 ml) drink. Thus, a single eight-ounce serving of such a calcium-fortified beverage would provide greater than about 10 percent of the recommended U.S. DV for calcium. In another embodiment, a calcium-fortified aqueous composition is provided containing about 30 to about 50 mg calcium from the amorphous calcium citrate salt per fluid ounce serving, and about 320 to about 400 mg calcium per eight fluid ounce (about 240 ml) drink. Thus, a single eight-ounce serving of such a calcium-fortified beverage would provide about 25 to about 40 percent of the recommended U.S. DV for calcium. In still another embodiment, a calcium-fortified aqueous composition is provided containing sufficient calcium from the amorphous calcium citrate salt per eight fluid ounce (about 240 ml) drink to provide at least about 50 percent of the DV level, and preferably at least about 100 percent of the DV level.

The amorphous water-soluble calcium citrate salts of this invention, even when used to provide high levels of calcium fortification, are typically present in instant beverage mixes and liquid food compositions at much lower concentration than the reaction mixtures from which they were formed. The comparatively dilute solutions that typify nutritional product applications greatly reduce and often eliminate the tendency of these amorphous salts to be transformed to an insoluble crystalline material. In addition, the preferred use of these ingredients in acidified beverage products containing citric acid or other food acids typically further reduces the tendency of the dissolved amorphous salts to be transformed to an insoluble crystalline material. By comparison, the citric acid or other food acids present in such preferred applications is typically not able to dissolve a significant amount of insoluble material produced by crystalline commercial calcium citrate salts when they are used at levels needed to provide effective fortification.

In another embodiment of the present invention, a method is provided to supplement dietary calcium intake in individuals by administering an effective amount of the amorphous calcium citrate salts of this invention, preferably in the form of a calcium-fortified liquid composition.

As will be appreciated from the descriptions herein, a stable, rapidly dissolving calcium citrate powder with high calcium content is provided which is useful in calcium fortified beverages and foods, including gelled or structured foods and beverages, to provide a highly functional and soluble dietary calcium source. The amorphous water-soluble calcium citrate fortified beverage drinks of this invention have excellent storage stability without calcium citrate sedimentation or turbidity. They also are highly palatable and are essentially free of unacceptable off-tastes or off-flavors, even at relatively high addition levels.

DETAILED DESCRIPTION

The present invention generally relates to the production of new calcium citrate salts under controlled conditions effective to provide an amorphous water-soluble salt product that dissolves rapidly in aqueous fluids to form clear, haze-free and sediment-free drinks and beverages. These new calcium citrate salts are highly useful calcium fortifying agents for beverages and foods. Unlike crystalline calcium citrate salts, such as tricalcium citrate salts, RTD beverages and reconstituted powdered beverages containing the amorphous calcium citrate salts of the present invention exhibit a clear, non-turbid appearance and remain sediment-free throughout their shelf life. Consequently, amorphous water-soluble calcium citrate compounds of the present invention provide a readily available nutritional calcium source which can be used in a wide variety of food products. The new amorphous water-soluble calcium citrate salts described in embodiments herein also are compatible with many common and otherwise useful additives used in food and beverage formulations. For instance, beverage formulations can include flavoring agents, sweeteners, acidulants, stabilizers, and so forth, without inducing haze formation from solid particle suspension, or sedimentation, of the calcium citrate salts.

In one aspect, the present invention relates to amorphous water-soluble calcium citrate salts of the formulas:

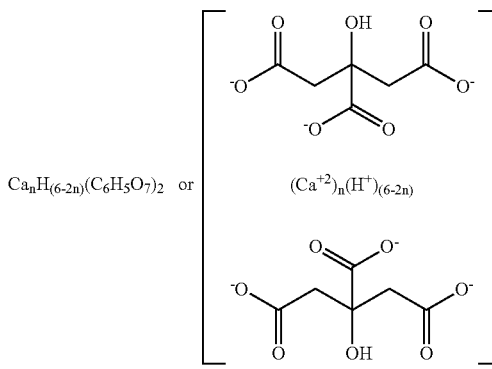

wherein "n" is a value of less than 2.5, preferably less than about 2.25, and more preferably about 1 to about 2. The "$C_6H_5O_7$" portion of the formula represents a citrate moiety.

The amorphous water-soluble calcium citrate salts of this invention are prepared by reacting a calcium compound with citric acid in an aqueous medium to produce calcium citrate having a calcium to citrate mole ratio of less than 2.5:2. The resulting reaction mixture is then quickly dried (or quickly frozen for drying at a later time) in order to separate and isolate amorphous calcium citrate as a dry powder. It is important that the amorphous water-soluble calcium citrate reaction salt is recovered from the aqueous reaction mixture as a dry amorphous material before it can be transformed into insoluble crystalline tricalcium citrate (TCC) or other water-insoluble calcium citrate salts. As shown in the examples below, both the condition of providing a calcium:citrate mole ratio of less than 2.5:2, and the condition of drying the reaction mixture soon enough after the salt-producing reaction, as detailed herein, to avoid reaction product transformation into water-insoluble calcium citrate salts, are important to ensure that the solid calcium citrate reaction product is recovered in an amorphous state. Preferably rapid drying techniques are also used to minimize the opportunity for crystallization of the reaction product during the drying operation. Suitable rapid drying techniques include, for example, freeze drying and spray drying.

Powdered forms of the amorphous water-soluble calcium citrate salts prepared having the mole ratio values prescribed herein are quickly and completely dissolve in water. Consequently, clear, haze-free, sediment-free aqueous compositions can be prepared with them. By contrast, calcium citrate salts that are either crystalline or have a calcium/citrate mole ratio of greater than 2.5:2 are observed to be noticeably water-insoluble, and liquid compositions formulated with them include undesirable solid (undissolved) calcium citrate particulate suspensions (yielding a hazy appearance and/or gritty texture) or sediments. Such undissolved forms of calcium, in addition to being visually and/or organoleptically undesirable, can reduce the amount of dietary calcium available in the food or beverage product as compared to the calcium species provided by the present invention.

In one embodiment, a calcium source and citric acid reactant are combined at room temperature (i.e., approximately 20 to 30° C.) within the above-prescribed mole proportions in an aqueous environment. Quickly after combining the calcium source and citric acid reactant, the resulting reaction mixture is dried (preferably using a rapid drying techniques) before a sediment or haze comprising crystalline calcium citrate can form and appear in the reaction mixture. The drying must occur shortly after the reaction mixture containing the calcium citrate reaction product is formed in order to prevent transformation of the amorphous calcium citrate product into less stable, water-insoluble crystalline forms of the salt. How quickly the drying should take place depends, at least in part, on the temperature. Generally and under refrigeration conditions, such rapid drying should be carried out within about 30 minutes, and preferably within about 15 minutes, of the reaction mixture formation. Generally and under ambient conditions, such rapid drying should be carried out within about 5 minutes, and preferably within about 2 minutes, of the reaction mixture formation. Alternatively, the reaction mixture can be quickly frozen (generally within about 5 minutes, preferably within about 2 minutes, and more preferably with about 1 minute of the reaction mixture formation) for later drying; once frozen, the reaction mixture should be dried under conditions which prevent or minimize thawing. In one embodiment, a rapid drying procedure comprising freeze drying or spray drying is used. Where freeze drying is used, the frozen solid piece or pieces obtained are comminuted into a powder form after freeze drying. Where spray drying is used, the calcium and citric acid reactant preferably are chilled at the time of their admixture and up until drying.

The calcium source or calcium-containing reactant is a calcium compound that reacts with citric acid in aqueous solution to form calcium citrate. These calcium compounds include calcium oxide, calcium hydroxide, calcium carbonate, or combinations thereof. Calcium hydroxide is preferred. The calcium source can be pre-slurried in water or added dry to the aqueous medium. Once the calcium compound and citric acid reactant are conveniently admixed in water, the reaction proceeds rapidly. The addition order of the reactant and aqueous concentrations thereof are not particularly limited as long as adequate stirring or agitation is provided to intermix the reactant within a short period of time; of course, the relative amounts of the calcium source and citric acid are controlled to obtain the desired mole ratio of calcium and citrate.

The above-identified subscript values "n," "(6n−2)," and "2" in the formulas for the amorphous calcium citrate of this invention can be obtained by controlling the relative amounts of the calcium-containing reactant and citric acid reactant used in making the amorphous salt. Temperature, reactant concentrations, agitation, or hold time before commencing drying or freezing are parameters in determining the physical characteristics of the final product. They are controlled in manners described herein to ensure that an amorphous calcium citrate can be obtained.

The reaction between the calcium source and citric acid is exothermic in nature. Therefore, preferably the reaction mixture is held in a reaction vessel or container that can be cooled by any conventional or convenient means for that purpose during the reaction and until dried. Generally it is preferred that the temperature be kept below about 30° C., preferably below about 10° C., and more preferably between about 0 and 5° C. during the reaction period.

To dry the reaction mixture, drying (preferably using a rapid drying technique) can be performed immediately, or the reaction mixture can be immediately frozen for later drying (preferably freeze drying). In either instance, the amorphous character of the calcium citrate product in the reaction mixture is preserved upon drying. The preferred method for drying is freeze drying. Using freeze drying, the reaction mixture, whether prefrozen or not, is placed into a conventional freeze dryer, and then dried, thereby obtaining the amorphous calcium citrate in solid form. The freeze dried solid calcium citrate product of this invention is preferably comminuted into powder form. Namely, the relatively large freeze dried solid(s) are pulverized into a flowable particulate suited for the calcium fortification applications for liquids and other foods contemplated in embodiments of this invention. For example, the amorphous calcium citrate salt product obtained by freeze drying can be ground or milled such that about 95 percent pass through a U.S. 100 mesh (about 150 micron) screen. Preferably, fine dusts are avoided since they can pose handling problems and are generally unnecessary for achieving rapid dissolution in aqueous solutions of the amorphous salt particles produced according to embodiments of this invention.

Alternatively, spray drying can be used to dry the amorphous calcium citrate of this invention. For spray drying, the calcium-containing reactant and citric acid are preferably pre-chilled before or during admixture (generally to below about 10° C. and preferably about 0 to about 5° C.), and the resulting chilled mixture is quickly spray dried before a sediment or haze comprising crystalline calcium citrate forms and appears in the reaction mixture. The calcium-containing reactant and citric acid again are added in the calcium:citrate mole ratio of less than about 2.5:2. Spray drying should be commenced soon after the completion of the calcium citrate producing reaction (generally within about 30 minutes or less) to minimize the chance of the reaction product transforming into a less water-soluble crystalline forms of calcium citrate, such as TCC and the like. Generally, the reaction mixture is spray dried at an inlet temperature of from about 400 to about 475° C. to deliver a dried free-flowing white powder.

The opportunities for undesirable crystalline calcium citrates to occur are primarily a function of the reaction mixture temperature, reactant concentrations, and hold or storage time parameters. Generally, the risk of crystallization of the reaction product increases with increasing reaction mixture concentrations, temperatures, and/or hold times before commencing the drying procedure. The limits on these parameters can be ascertained empirically in a straightforward manner for a given reaction system. In any event, the reaction mixture conditions should be monitored and adjusted to avoid occurrence of water-insoluble crystalline calcium citrates in the reaction product. The presence of water-insoluble crystalline calcium citrates will be visually noticeable as the reaction mixture will have a slurried constitution in which solid calcium citrate crystalline particles are suspended in the fluid.

The dry powdered amorphous water-soluble calcium citrate salts obtained by the above-described techniques generally contain less than about 5 percent water, and more typically less than about 2 percent water. The amount of water present does not interfere with the loose, freely flowable properties of the material. Calcium citrate products made by methods described herein are generally free of large clumps; if necessary, however, large lumps can be removed using grinding or sieving techniques. The present new salts are slightly to moderately acidic, have a low moisture content, and do not undergo any significant gain or loss of water during storage. The unique amorphous water-soluble calcium citrate salt products of this invention also generally have a bulk density of about 0.1 to about 0.7 g/cc, with about 95 percent passing through U.S. 100 mesh (or 150 microns), and are freely-flowable, white to yellow-white powders. In one embodiment, an approximately 1 percent calcium citrate salt in deionized water solution at approximately 25° C. has a pH value from about 3 to about 5, and preferably from about 3.5 to about 4.5.

In the practice of the present invention, the amorphous water-soluble calcium citrate, and, if desired, other solutes and additives are added to an aqueous medium in preparing a nutritional drink or beverage; the level of the amorphous calcium citrate and other additives should be less than their respective solubility limits, so that no sediment or solid residue is deposited or suspended in the composition. The amorphous water-soluble calcium citrate salts having the mole ratio prescribed herein generally can be wholly dissolved in liquid compositions at robust calcium fortification levels without imparting undesirable taste, mouthfeel, visual appearance, or odor in the drink or beverage. Chalky or gritty solutions containing a noticeable haze or sedimentation of the calcium citrate or other solutes are avoided. Instead, clear and smooth calcium-fortified drinks and beverages can be provided in the present invention.

The amorphous water-soluble calcium citrate generally is added to liquid compositions, such as RTD beverages and reconstituted powdered drinks, on an elemental calcium weight basis, at a rate of about 3 mg or more, particularly from about 3 mg to about 250 mg, more particularly from about 12.5 mg to about 125 mg, per fluid ounce of the beverage. An eight ounce serving of a calcium-fortified beverage prepared according to the invention delivers approximately 2 to approximately 200 percent of the DV for calcium (about 1000 mg/day). The amount of amorphous calcium citrate added to solution to achieve the above-indicated calcium addition levels can be readily calculated and implemented. In the case of the reconstituted form made by dissolving a powdered mix in liquid, formulation instructions can be provided on the packaging for consumers to guide them on how to implicitly or explicitly formulate this calcium concentration. Using these introduction levels of the calcium, as obtained from amorphous calcium citrate, a typical eight fluid ounce serving can provide a rich source of an individual's DV for calcium.

For either RTD or reconstituted powdered beverages according to the present invention, the primary ingredient will be the amorphous water-soluble calcium citrate alone or in combination with a flavoring material, and a liquid in which the calcium citrate and, if present, the flavoring ingredient, are soluble. Other soluble and edible ingredients can be added as desired so long as they do not adversely affect the organoleptic properties.

The liquid in which the calcium citrate and flavoring material, and any other ingredients, is dissolved is preferably water based. Water containing a relatively small amount (generally less than about 20 percent) of alcohol can also be used in appropriate products. Water-based liquid vehicles are preferred in the practice of the invention. The proportion of liquid generally will be that sufficient to permit solubilization of the ingredients and also sufficient to permit the desired strength/dilution of the flavoring agents to be achieved. Generally, the proportion of water used in fruit drink beverages encompassed by the invention, whether RTD or reconstituted forms, will be about 50 to about 99 percent.

For fortified fruit-flavored beverages, water-soluble and water-dispersible flavoring agents can be used, including commercially available flavoring agents for fruit drinks. Common fruit flavoring materials useful in this invention include, for example, orange oil, lime oil, lemon oil, and so forth. Other flavoring materials also can be found in published formulation recipes for fruit drinks. Also, natural fruit juice concentrates can be added to the beverages to provide or accentuate the fruit flavoring desired. These concentrates typically will be in liquid, pulped, or syrup forms. A fruit juice "concentrate" generally contains at least about 45 percent fruit juice. In another embodiment, a flavoring agent is contained in the beverage which imparts a grapefruit, kiwi, raspberry, cherry or other fruit flavor.

Food colorings also can be added to the inventive beverages, such as U.S. Certified Food Colors. Preservatives also can be added to the inventive beverages, such as sodium benzoate, ascorbic acid, propylene glycol, and the like. Also, in the case of the dry powdered beverage mixes of the invention, users often can be expected to use tap water to reconstitute the beverage. In that tap water often is slightly alkaline due to the presence of dissolved mineral salts therein, edible acids, such as citric acid, malic acid, and the like, also can be included to neutralize the alkalinity of tap water or for other purposes.

The beverages of this invention also can contain a sweetener. Suitable sweeteners include, for example, sucrose, glucose, fructose, hydrolyzed corn starch, maltodextrin, corn syrup solids, lactose, high fructose corn syrup, fructooligosaccharides, artificial sweeteners, and the like as well as mixtures thereof. Suitable artificial sweeteners include, for example, aspartame, sucralose, saccharine, cyclamates, acesulfame potassium, and the like as well as mixtures thereof. In the case of powdered dry mixes, the sweetener generally will be present in granulated form in the mix prior to reconstituting the drink. The amount of sweetener can vary, but generally, if present, is in the range of from about 5 to about 25 percent of the RTD or reconstituted beverage.

In that embodiments of the invention encompass nonfat beverage products, the desirable mouthfeel that would normally be provided by fat content can instead be provided, at least to some extent, by non-fat stabilizers, including celluloses (e.g., carboxymethyl cellulose, sodium carboxymethyl cellulose, hydroxymethyl cellulose, hydroxypropyl methyl cellulose, cellulose gel) and/or xanthan gum, guar gum, gum arabic, and so forth. In reconstituted powdered beverage mixes of the invention, the amount of such stabilizers generally can be from about 0.1 to about 15 percent.

Fat also optionally can be introduced as an ingredient of the beverages. Suitable fats include, for example, soy oil, hydrogenated soy oil, fractionated coconut oil, high oleic safflower oil, corn oil, canola oil, and the like as well as mixtures thereof. For example, soy drinks can be prepared as RTD beverages or as beverages reconstituted from powdered dry mixes according to embodiments of the invention.

The powdered beverage mixes of the present invention are formed from a dried flavor base containing the calcium citrate salts of this invention. The flavor base can be dried by conventional means known to the art, such as spray drying, evaporative drying, vacuum drying, or freeze drying. Preferably, the drying method provides rapidly dissolvable particles. Sugar, and/or stabilizers such as cellulose and the like, also can be used as carriers for other ingredients of the dried flavor base. Additional optional ingredients include one or more of other common ingredients for beverages (e.g., functional agents like flow agents such as silica, or caffeine, and so forth). For health drinks, a vitamin/mineral premix also could be included.

Powdered beverage mixes include fruit flavored powdered drinks and soy "milk" beverages. RTD beverages include fruit flavored drinks and soy "milk" drinks. The beverages fortified according to this invention also can be frozen.

A soluble, dry powdered beverage mixture according to one illustrative, non-limiting, embodiment of the invention, comprises, on a dry weight basis: about 5 to about 50 percent amorphous water-soluble calcium citrate and about 0.1 to about 20 percent flavoring agent. In one embodiment, when reconstituted from a powdered mix, or as prepared directly as an RTD, the liquid composition provided contains the calcium citrate in an amount, based on calcium content, providing at least about 1 percent of the DV for calcium per fluid ounce of the liquid composition; a flavoring concentrate in an amount of about 0.02 to about 20 percent; and water in an amount of about 50 to about 95 percent. In the instance of powdered beverage mixes, instructions can be provided on the product container which instruct a consumer how to formulate a liquid composition that contains these ingredients in such proportions. The ingredients of the inventive beverage compositions are mixed with the liquid vehicle with stirring and agitation to the extent needed to dissolve the ingredients and ensure a substantially uniform dispersion of the ingredients is achieved in the liquid carrier or vehicle.

As discussed above, the beverages that can be fortified according to this invention include powdered beverage mixes and ready-to-drink (RTD) beverages. Whether prepared as a RTD or reconstituted beverage, it has been observed and demonstrated that the calcium citrate used in fortifying beverages according to embodiments of this invention is wholly dissolved and nutritionally available.

The Examples that follow are intended to illustrate, and not to limit, the invention. All percentages used herein are by weight and the ratios of calcium to citrate are expressed as mole ratios, unless otherwise indicated.

EXAMPLES

Example 1

A series of calcium citrate salts was produced according to the embodiments of the invention for the purpose of identifying a practical upper limit of calcium:citrate mole ratio that can be easily produced in amorphous form while preventing significant solidification, crystallization, or sedimentation of the reaction mixture prior to drying. Powders having calcium:citrate mole ratios of 1:2 (monocalcium citrate or MCC), 1.5:2 (sesqui-calcium citrate or SCC), 2:2 (dicalcium citrate or DCC), 2.25:2, 2.4:2, 2.5:2, and 3:2 (tricalcium citrate or TCC), respectively, were separately produced by quickly pouring room temperature (about 22° C.) calcium hydroxide suspensions (7.4 to 22.2 g in 100 g water) into room temperature citric acid solutions (38.4 g in 100 g water), stirring vigorously for several seconds or until the hydroxide completely dissolved to form clear yellow-green solutions, quickly pouring the solutions into trays, immediately freezing via direct addition of liquid nitrogen to prevent formation of insoluble TCC or any other solid material, then freeze drying to obtain white granules that were easily comminuted to fine powders. The higher the calcium:citrate mole ratio used and the higher the reactant concentration, the faster the initially clear calcium citrate solutions began to haze, presumably from the onset of TCC formation.

Without desiring to be limited to theory, it is thought that formation of TCC, even at low calcium:citrate ratios, can occur via thermodynamically favorable disproportionation reactions due to the high solubility product constant of TCC. This would explain why a wide range of commercial calcium citrate salts obtained for evaluation in calcium fortified beverages all contained significant amounts of insoluble matter, presumably TCC, and immediately formed an unsightly precipitate in water.

All solutions formulated with a calcium:citrate mole ratio up to 2.25:2 were prepared and frozen without visible haze or sediment formation when treated in the manner described. However, solutions that were allowed to stand for longer than about 30 minutes produced large amounts of sediment (i.e., crystalline material). The 2.5:2 mole ratio solution, prior to freezing, seemed to produce a small amount of TCC in the form of suspended haze, despite rapid handling. The 3:2 mole ratio solution began to precipitate crystalline TCC very rapidly, seemingly even before all of the calcium hydroxide dissolved, making production of a sediment-free amorphous powder virtually impossible using the present manufacturing techniques. Although these experiments were performed using calcium hydroxide as the calcium source, calcium oxide and calcium carbonate also can be used as the calcium source.

The 2:2 mole ratio calcium citrate powder was examined using light microscopy to confirm the presence of a non-crystalline, amorphous structure. Micrographs were obtained to demonstrate the structural differences between this amorphous 2:2 mole ratio calcium citrate powder and a conventional crystalline TCC reference product (TCC tetrahydrate manufactured by Fortitech Inc.). The two materials had very different structural features when viewed under magnification with normal light. The two materials were then observed using polarized light. The commercial TCC exhibited essentially complete birefringence, thereby confirming a crystalline structure containing (at most) an insignificant amount of amorphous matter. The 2:2 mole ratio calcium citrate powder exhibited virtually zero birefringence under polarized light, thereby confirming an amorphous structure containing (at most) an insignificant amount of crystalline matter (i.e., less than one percent).

Addition of 240 ml room temperature water to 2 g of the 2:2 mole ratio calcium citrate powder (bulk density of about 0.18 g/cc) produced an instantly dissolving clear solution, providing 350 mg calcium per eight fluid ounce serving. The solution remained completely free of haze and sediment for at least two days of storage at room temperature. Similar or even better results were obtained from the salts prepared having calcium:citrate mole ratios lower than 2:2, even when dissolved in water at higher concentrations.

The 2.25:2 and 2.4:2 mole ratio calcium citrate powders dissolved completely in water (at levels sufficient to provide 350 mg calcium per eight fluid ounce serving) to form clear solutions that were free of sediment for at least six hours. These solutions, however, produced a very small amount of fine sediment overnight (i.e., just visible). These powders, in spite of the sediment produced, would provide very acceptable performance in many, if not most, food applications, including instant beverage mixes and acidified RTD beverages.

The 2.5:2 mole ratio calcium citrate powder (in an amount sufficient to provide 350 mg calcium per eight fluid ounce serving) dispersed completely in water, but a small undissolved portion formed a faint milky haze that began to slowly produce fine sediment after several minutes. This behavior might also be acceptable in some situations (i.e., opaque instant beverage mixes), but appears to represent a practical upper limit for applications that require high levels of soluble calcium and/or require a sediment-free transparent appearance.

The 3:2 mole ratio calcium citrate powder (added at levels sufficient to provide 350 mg calcium per eight fluid ounce serving) did not completely disperse in water; it formed a hazy suspension along with a small amount of fine sediment that gradually increased over time. Both the 2.5:2 and 3:2 mole ratio calcium citrate solutions produced very large amounts of fluffy white sediment when allowed to stand overnight at room temperature. By comparison, the crystalline commercial 3:2 mole ratio TCC reference material (bulk density of 0.45 g/cc) did not completely disperse in water under the same conditions and immediately produced a large amount of a coarse, gritty white sediment. Even a crystalline commercial 1:2 mole ratio MCC product (calcium citrate monohydrate manufactured by Dr. Paul Lohmann GMBH, Germany) did not completely disperse in water in an attempt to produce a 350 mg calcium per eight ounce serving size. It immediately produced a large amount of coarse, gritty white sediment that took several days to completely dissolve at room temperature.

Powders prepared according to the present invention, as described above, were added to water at a level of 1 percent to measure pH and assess initial solution appearance. The crystalline commercial 3:2 mole ratio TCC reference material was included for comparison. Results are provided in the following table:

| Calcium:Citrate Mole Ratio | Calcium Content (%) | Solution pH | Initial Solution Appearance |
|---|---|---|---|
| 1:2 | 9.5 | 3.4 | No haze; no sediment |
| 1.5:2 | 13.6 | 3.8 | No haze; no sediment |
| 2:2 | 17.4 | 4.1 | No haze; no sediment |
| 2.25:2 | 19.2 | 4.3 | No haze; no sediment |
| 2.4:2 | 20.2 | 4.4 | No haze; no sediment |
| 2.5:2 | 20.9 | 4.5 | Slight haze; some sediment (fine) |
| 3:2 | 24.1 | 5.4 | Moderate haze; more sediment (fine) |
| 3:2* | 21.1 | 5.9 | Milky haze; most sediment (coarse) |

*Crystalline commercial 3:2 mole ratio TCC reference material

In summary, the goal of creating amorphous calcium citrate salts that can be instantly and completely dissolved in water without production of haze or sediment and which can provide substantial amounts of calcium was achieved with calcium:citrate mole ratio below 2.5:2.

Example 2

As an alternative to freeze drying, an amorphous 2:2 mole ratio calcium citrate salt, using the same ingredients as in Example 1, was also successfully produced via spray drying (i.e., pilot scale drying using standard operating conditions and procedures). In this case, chilled calcium hydroxide and citric acid solutions were combined and rapidly spray dried before solidification or sediment formation could occur. Addition of 240 ml room temperature water to 2 g of this fine white powder produced an instantly dissolving clear solution, providing 350 mg calcium per eight ounce serving, that remained completely free of sediment for at least three days at room temperature. In a large scale commercial process, the citric acid and calcium hydroxide (or other suitable reagents) would be beneficially combined just prior to spray drying to limit the potential for solidification or sediment formation.

Based on the successful production of an amorphous 2:2 mole ratio calcium citrate salt on a pilot plant scale, the same general procedure was scaled up using a larger spray dryer. Several identical batches of citric acid solution and slurried calcium hydroxide suspension were prepared using the following procedure. Citric acid (1 kg) was dissolved in 2.6 liters water. Calcium hydroxide (385.5 g) was separately slurried in 2.6 liters water. All batches were chilled to a temperature of 4° C. using refrigeration.

One batch of the chilled citric acid solution was poured into a mix tank jacketed with cooling water and one batch of calcium hydroxide suspension was added with stirring. In less than one minute, the mixture cleared to form a yellowish solution and the temperature increased to 9° C., indicating that chemical reaction to form 2:2 mole ratio calcium citrate had occurred. The clear solution was immediately pumped into a semi-works scale spray dryer, fitted with an atomizing nozzle, at a flow rate of about 0.5 kg per minute. Additional batches of citric acid solution and calcium hydroxide suspension were similarly added to the mix tank as needed to prevent complete emptying. A sample of fine white powder was collected from the spray dryer after ten minutes of operation. The powder had an amorphous structure and rapidly dissolved in cold water without haze or precipitate to provide a solution having 350 mg calcium per eight fluid ounces. After a further fifteen minutes, the cooling water was shut off from the jacketed mix tank. A sample of powder collected from the spray dryer after thirty minutes did not dissolve completely in water due to the presence of a significant amount of crystalline calcium citrate. In less than one hour, the atomizing nozzle and pipe between the mix tank and the spray dryer became plugged with an accumulated deposit of insoluble crystalline calcium citrate. This example demonstrates the benefit of maintaining calcium citrate solutions at low temperature when spray drying and the necessity of rapidly drying to prevent detrimental solidification and precipitation during processing.

Example 3

This example illustrates the preparation of an amorphous salt having calcium:citrate mole ratio of 1:2 and which contains nutritive levels of iron, potassium, and calcium. Iron sulfate heptahydrate (0.54 g), potassium hydroxide (10.20 g), and citric acid (18.46 g) were sequentially dissolved in 100 g water. Calcium hydroxide 3.70 g was slurried in 100 g water and poured into the solution containing citric acid at room temperature (about 22° C. The resulting solution had a light yellow color and was clear and sediment free. The solution was poured into a tray, rapidly frozen by direct addition of liquid nitrogen, and then freeze dried.

The dried granular salt had a light yellow color and was easily ground to a fine powder using mortar and pestle. The powder (1.4 g) dissolved instantly and completely in eight fluid ounces of cold water to provide a liquid composition containing FDA good-source levels of iron (about 5 mg), calcium (about 100 mg), and potassium (about 350 mg). This solution had a pH of 5.7 and an appealing light yellow appearance and remained free of haze and sediment for at least eight hours. Addition of 5 g granular sugar to the solution produced a nutritive beverage having pleasant citrus-like flavor and appearance.

Example 4

The freeze-dried 2:2 mole ratio amorphous calcium citrate salt of Example 1 was used to impart a FDA excellent-source level of calcium to two commercial instant beverage mixes. One sample of the amorphous salt (2.0 g) was combined with 17.0 g sweetened Cherry Kool-Aid® powdered instant drink mix in a 400 ml beaker. The powdered drink mix contained sugar, fructose, citric acid, calcium phosphate (not a significant source of calcium), artificial flavor, artificial colors, and ascorbic acid. Another sample of the amorphous salt (2.0 g) was combined with 2.0 g artificially-sweetened Lemon CRYSTAL LIGHT® powdered instant drink mix and placed in a 400 ml beaker. The powdered drink mix contained citric acid, potassium citrate, maltodextrin, aspartame, magnesium oxide, natural flavor, lemon juice solids, acesulfame potassium, artificial colors, and BHA.

Each of the calcium-fortified powdered mixtures were combined with eight fluid ounces of cold water to produce a beverage having excellent flavor and appearance. In both cases, the amorphous calcium citrate salt dissolved immediately, without the need for stirring, when water was added to each of these calcium-fortified powdered drink mixes. Each reconstituted beverage provided 350 mg calcium per serving and remained free of sediment for at least 24 hours.

For comparison purposes only, similar beverages were prepared by substituting 1.7 g of the crystalline TCC reference product in place of the amorphous salt in each of these powdered drink mixes. In each case, large amounts of coarse gritty sediment were formed immediately; the sediment completely covered the bottom of the beakers to a depth of about a millimeter. The sediments did not dissolve with rapid stirring or with the passage of time. The crystalline calcium citrate salt combined with these powdered drink mixes did not provide effective calcium fortification; the beverages had unacceptable appearance and overall quality.

Example 5

Fortified RTD beverages were formulated with several forms of calcium citrate. The visual appearance, flavor, and stability of the products were evaluated over a seven-month period by an experienced panel. Identical samples of each fortified beverage were prepared for shelf life testing under both ambient (22° C.) and refrigerated (4° C.) storage conditions.

The freeze dried amorphous 2:2 mole ratio calcium citrate salt (17% calcium) of Example 1 was successfully used to fortify a ready-to-drink sugar-free lemon-flavored beverage (CRYSTAL LIGHT®) with 350 mg calcium per eight fluid ounce serving ("excellent source of calcium" level). To formulate the calcium-fortified powdered mix, eight fluid ounces of commercial CRYSTAL LIGHT® RTD beverage mix was mixed thoroughly with 2 g of the freeze dried amorphous 2:2 mole ratio calcium citrate salt. The calcium-fortified beverage remained sediment free and exhibited acceptable flavor and appearance throughout the seven-month shelf life evaluation period at both room temperature and under refrigeration conditions.

However, when crystalline commercial MCC monohydrate (9 percent calcium) and crystalline TCC tetrahydrate (21 percent calcium) salts were used in place of the amorphous 2:2 mole ratio calcium citrate salt (in amounts designed to provide the same level of calcium), the resulting beverages otherwise formulated in the same manner were unacceptable due to noticeable sediment formation upon admixture of the ingredients.

The same freeze dried amorphous 2:2 mole ratio calcium citrate salt of Example 1 was used to similarly fortify a ready-to-drink thermally processed sweetened orange-flavored beverage (TANG®). To formulate the calcium-fortified beverage, eight fluid ounces of a commercial TANG® beverage was mixed thoroughly with 2 g of the freeze dried amorphous 2:2 mole ratio calcium citrate salt. The resulting calcium-fortified beverage was exposed a high temperature short time (HTST) sterilization procedure prior to bottling. The calcium fortifying agent remained in solution throughout the thermal processing operation without any apparent loss of solubility or sediment formation.

While the invention has been particularly described with specific reference to particular process and product embodiments, it will be appreciated that various alterations, modifications and adaptations may be based on the present disclosure, and are intended to be within the spirit and scope of the present invention as defined by the following claims.

What is claimed is:

1. A method for producing an amorphous water-soluble calcium citrate salt, comprising forming a reaction mixture by reacting a calcium compound with citric acid in an aqueous solution at a temperature of less than about 10° C. to form a calcium citrate reaction product which has a mole ratio of calcium to citrate in the range of from about 1:2 to less than 2.5:2, and spray drying the reaction mixture at a temperature of less than about 10° C. effective to provide the amorphous water-soluble calcium citrate salt in solid form, wherein the amorphous water-soluble calcium citrate salt, when dissolved in water to provide to about 10 mg calcium per fluid ounce, does not form a visible haze or sediment for at least about 2 days at ambient temperatures.

2. The method of claim 1, wherein the spray drying is performed before the reaction mixture stands for a period of time at which a water-insoluble calcium citrate salt forms in the reaction mixture.

3. The method of claim 1, wherein the calcium compound is selected from the group consisting of calcium oxide, calcium hydroxide, calcium carbonate, and combinations thereof.

4. The method of claim 1, wherein the mole ratio of calcium to citrate is less than about 2.25:2.

* * * * *